United States Patent [19]
Guttag

[11] Patent Number: 5,851,611
[45] Date of Patent: Dec. 22, 1998

[54] MULTI-LAYERED STORAGE CONTAINER

[75] Inventor: Alvin Guttag, 415 Russell Ave., Apt. 108, Gaithersburg, Md. 20877-2845

[73] Assignee: Alvin Guttag, Gaithersburg, Md.

[21] Appl. No.: 462,031

[22] Filed: Jun. 5, 1995

[51] Int. Cl.$^6$ ............................. G01N 21/00; B32B 27/00
[52] U.S. Cl. ..................... 428/35.7; 428/36.6; 428/483; 428/517; 428/518; 428/523; 206/484; 206/484.2; 206/807; 422/55
[58] Field of Search ..................................... 428/35.7, 518, 428/36.6, 36.7, 483, 524, 517; 206/484, 807, 484.2; 422/55, 58

[56] References Cited

U.S. PATENT DOCUMENTS

| | | | |
|---|---|---|---|
| 3,579,624 | 5/1971 | Guttag | 264/171.14 |
| 4,098,577 | 7/1978 | Halpern | 206/484 |
| 4,952,426 | 8/1990 | Guttag | 427/258 |
| 5,120,089 | 6/1992 | Guttag | 283/71 |
| 5,234,732 | 8/1993 | Versic et al. | 428/35.7 |

*Primary Examiner*—Rena L. Dye
*Attorney, Agent, or Firm*—Pillsbury Madison & Sutro LLP

[57] ABSTRACT

One aspect of the present invention reveals a multi-layered storage container that changes color in response to acid gases. The storage container is comprised of at least one layer of a plastic and at least one layer of a gas-barrier polymer. Furthermore, the multi-layered storage container is provided with a color-changing indicator to show the presence of acidic gases. The other aspect of the present invention reveals a diaper which, as the result of chemical and/or electrical processes, can indicate when the diaper is wet.

15 Claims, No Drawings

MULTI-LAYERED STORAGE CONTAINER

BACKGROUND OF THE PRESENT INVENTION

One aspect of the present invention is for a multi-layered storage container that changes color in response to acid gases. The storage container can be used to protect items like stamps, photographs, museum pieces and the like. The other aspect of the present invention is for a diaper which, as the result of chemical and/or electrical processes, can indicate when the diaper is wet.

In regard to the first aspect, the present invention relates to the protection of items like stamps, photographs, museum pieces and the like with use of multi-layered storage containers that change color in response to degradation of the container material. The conventional storage containers like stamp mounts and pockets for postal stationery are frequently made of a common plastic like polyethylene, polyethylene terephthalate, polystyrene, polypropylene, and the like. However, these plastics have the disadvantage of porosity to gases like water vapor, oxygen, as well as acidic gases like carbon dioxide, hydrogen chloride, sulfur dioxide, and sulfur trioxide. Acidic gases can attack the item being stored (like the stamp or photograph) over long periods of time.

Fortunately, vinylidene chloride polymers such as polyvinylidene chloride, vinylidene chloride-acrylonitrile copolymer, vinylidene chloride-vinyl chloride copolymer (otherwise known as Saran®), have superior resistance to the transmission of many gases like oxygen and carbon dioxide. However, over long periods of time, Saran and many other halogen-containing polymers slowly degrade and give off, for example, hydrogen chloride. Vinyl chloride-based polymers such as, for example, polyvinyl chloride and vinyl chloride-vinyl acetate copolymer have the same disadvantage.

In regard to the second aspect, the present invention also relates to moisture-indicating diapers. A need exists to make it easier for adults to detect when a baby's diaper needs to be changed. Despite the relatively good quality of modern disposable diapers compared to those of the past, disposable diapers still do not allow the adult to check conveniently the wetness of the diaper. If the diaper is not changed quickly, of course, the baby may suffer causing suffering in the responsible adult as well.

SUMMARY OF THE PRESENT INVENTION

The first aspect of the present invention reveals a multi-layered storage container that changes color in response to acid gases. The storage container is comprised of at least one layer of a plastic and at least one layer of a gas-barrier polymer. Furthermore, the multi-layered storage container is provided with a color-changing indicator to show the presence of acidic gases.

In one embodiment of the invention, the plastic can be selected from the group comprising polyethylene, polypropylene, polyethylene terephthalate or polystyrene.

In another embodiment, the gas-barrier polymer can be selected from the group comprising vinylidene chloride-based polymer or vinyl chloride-based polymer.

Furthermore, the vinylidene chloride-based polymer can be selected from the group comprising polyvinylidene chloride, vinylidene chloride-acrylonitrile copolymer or vinylidene chloride-vinyl chloride copolymer and the vinyl chloride-based polymer can be selected from the group comprising polyvinyl chloride or vinyl chloride-vinyl acetate copolymer.

In another embodiment, the color-changing indicator can be selected from the group comprising litmus, methyl orange, bromphenol red or bromthymol blue.

In yet another embodiment, the color-changing indicator shows the presence of acidic gases selected from the group comprising carbon dioxide, hydrogen chloride, sulfur dioxide or sulfur trioxide.

The second aspect of the present invention reveals a diaper comprising means for indicating when the diaper is wet, wherein the means can be selected from the group comprising chemical means or electrical means.

In one embodiment, the chemical means for indicating when the diaper is wet comprises a color-changing indicator that changes color when wet. Furthermore, the color-changing indicator can be selected from the group comprising anhydrous cupric sulfate, cupric sulfate monohydrate, cupric sulfate pentahydrate or fluorescent dye.

In another embodiment, the chemical means for indicating when the diaper is wet comprises a color-changing indicator that changes color in response to pH change.

In another embodiment, the electrical means for indicating when the diaper is wet comprises conductors and a power source. Furthermore, the conductors can be selected from the group comprising conductive polymers or metal-polymer blends.

In another embodiment, the electrical means for indicating when the diaper is wet further comprises exogenous electrolytes. Furthermore, the exogenous electrolytes can be selected from the group comprising sodium chloride, potassium chloride, copper sulfate, boric acid, potassium hydrogen phthalate or potassium dihydrogen phosphate.

In yet another embodiment, the electrical means for indicating when the diaper is wet generates a visible or audible signal when the diaper is wet. Furthermore, the visible signal can be white light or colored light.

DESCRIPTION OF THE PRESENT INVENTION

Objects of the present invention include improving the ability to protect items like stamps, photographs museum pieces, etc. while stored over long periods of time.

The present inventor has found that items like philatelic items and photographs, as well as museum pieces can be preserved for longer period of times if stored in containers made of multi-layered films or sheets comprising at least one layer of a plastic and at least one layer of a gas-barrier polymer. Moreover, the plastic or the gas-barrier layer can be provided with a color-changing indicator to show when acidic gases are being generated by degradation of the gas-barrier polymer (or from any other source) and alert a person of the danger.

The color-changing indicator can be, for example, litmus (red color at pH 4.5 and below), methyl orange (red color at pH 3.1 and below), bromphenol red (yellow color at pH 5.2 and below), bromthymol blue (at pH 6.0 and below). Other color-changing indicators can be used as known to those skilled in the art depending on the desired pH necessary to give warning of undesired acidity. Other exemplary indicators include those described in *The Merck Index,* 11*th Edition* (Merck & Co.) pages MISC110–112, the complete disclosure of which is incorporated herein by reference and relied upon.

Many items can be stored by means of the present invention, and in particular, those items like philatelic items that are sensitive to acidity over a long term. The term "philatelic item" is defined for purposes of the present invention according to Guttag in U.S. Pat. No. 5,120,089, col. 2 lns. 32–42, the complete disclosure of which is incorporated herein by reference and relied upon. Exemplary plastics and gas-barrier polymers are respectively shown by Guttag in U.S. Pat. Nos. 4,952,426, col. 2, lines 39–62 and 3,579,624, col. 5, lines 51–65, the complete disclosures of which are herein incorporated by reference and relied upon. Among the plastics mentioned in U.S. Pat. No. 4,952,426 which can be used in the present invention are polyethylene, polypropylene, ethylene-mono-olefin copolymer, polyamylene, linear polyester and polycarbonate. Among the plastics mentioned in U.S. Pat. No. 3,579,624 which are useful in the present invention are hydrocarbon polymers and mono-olefins having two to six carbon atoms. Preferable gas-barrier polymers are halogen-containing polymers and saran.

To help ensure that no acidic gas reaches the stored philatelic item or photograph, two or more layers of the plastic can be layered around each side of the gas-barrier polymer. If a plurality of plastic layers are used, the plastic layers can be made of the same or different plastic material. The color-changing indicator can be in any of the layers. Mixtures of indicators can be used.

The storage container can be open at one end. The open end can be closed by, for example, using a velcro-like closure or a tongue-and-groove closure as found in common sandwich bags. These closures can be opened and closed repeatedly. The gas-barrier polymer like saran can optionally be included in the end closure or can terminate prior to the end closure and thus not contact the atmosphere at all. The storage container can be in the form of a storage pocket.

Objects of the present invention also include simplifying the detection of wetness in products designed to absorb biological excretions (such as diapers, for example). The invention can be used with diapers for infants and with incontinent adults. Such simple detection can be accomplished in several ways. For example, a color-changing indicator that will change color when wet can be incorporated into layers of the diaper. In addition, pH change caused by urine or defecation can also change the color of the indicator.

A diaper can be impregnated with, for example, powdery anhydrous cupric sulfate (pale greenish white or pale grayish white), cupric sulfate monohydrate (white), or cupric sulfate pentahydrate (pale blue). All of these materials change from their almost colorless or pale colored state to a very intense blue colored state when they become wet. Other exemplary indicators include fluorescein sodium which has an orange-red color in dry form but an orange-yellow color with intense yellowish-green fluorescence in wet form. Eosin can also be used. In place of fluorescein sodium or eosin there can be employed any other fluorescent dye that changes color when wet to tell when a diaper needs changing.

Alternatively, the diaper can be impregnated with an indicator which changes color in response to pH. For example, indicators that change color when in contact with the ammonia or ammonium hydroxide present in urine can be used. Exemplary indicators of this type are again described in *The Merck Index, 11th Edition* (pages MISC110–112). Those indicators which change color on the alkaline side due to ammonia or ammonium hydroxide are preferred. It is not necessary to use just one indicator. Mixtures of indicators can also be used as described in *The Merck Index, 11th Edition* page MISC112, especially those indicators having a transition pH on the alkaline side.

The indicators can be incorporated in commercially available diapers like, for example, Pampers®, Luvs®, or Huggies®. The diapers can be made by various conventional diaper preparation methods as known to those skilled in the art. For example, the methods described in the references cited mentioned by Guttag in U.S. Pat. No. 5,346,929, column 3, lines 45–48, as well as those methods mentioned in U.S. Pat. Nos. 5,137,534; 5,026,364; 4,938,755; 4,909,803; Re. 32,649; 4,834,735; 4,816,025; 4,808,178; 4,795,454; 4,743,246; 4,695,278; 4,515,595; 4,798,603; 4,753,649; 4,704,116, the complete disclosures of which are hereby incorporated by reference and relied upon.

It is not necessary to have the entire diaper impregnated or treated with the indicator. If desired, only a small area of the diaper such as, for example, the area where wetness is most likely to occur first can be treated.

Also, it is not necessary to treat all layers of the diaper. For example, it may be desirable not to treat the layer of diaper closest to the skin of the baby. This should help to avoid possible allergic reaction by the baby to the indicator. Instead, only one or more of the remote layers need be treated with the indicator, either partially or over the entire surface. The indicator should be non-toxic and non-irritating to human skin. The diaper should be constructed so that the layer or layers containing the indicator should be visible on the outside so that the change in indicator color can be seen easily.

It is also possible to treat different layers of the diaper with different color indicating materials. Thus each layer could be treated with a different color changing indicator. Alternatively, the first layer (the layer closest to the baby's skin) could be treated with one color changer and the remaining layer or layers treated with a different color changer, thus giving the caretaker a choice as to when to change the diaper. Also, if the first layer is thick, the indicator could be used in only the upper part of the layer (the portion remote from the baby's skin) or one indicator could be used in the lower part of the layer and a different indicator could be used in the upper part of the layer.

Diapers are constructed from absorbent, and preferably highly adsorbent, materials. The highly adsorbent material can be any of the materials described in the U.S. Patents already incorporated by reference herein and relied upon. For example, the adsorbent material can be a hydrogel-forming polymer, a polysaccharide, wood pulp fiber, or the like. The indicator can be mixed into the highly adsorbent material by any conventional method of mixing known to those skilled in the art. For example, the indicator can be sprayed on as a powder, or the indicator can be applied to the surface of the absorbent material.

In an alternative embodiment, electric means of indication are used rather than chemical means for detecting wetness in a diaper. When the diaper is wet, it will become a conductor of electricity because urine contains endogenous electrolytes. Moreover, one or more exogenous electrolytes can be incorporated in the diaper in order to enhance the electrical conductivity of the diaper when wet.

Thus, when a diaper is wet, an electric circuit will be completed, e.g., a circuit comprising a power source and conductors. The power source can be a battery equipped with thin conductive wire. The circuit can be designed by means known to those skilled in the art with the proviso that completing the circuit does not result in shock or other harm to the baby, of course.

Completion of the circuit can cause a visible or audible signal to emit from the diaper which is readily detected by adults. Visible light can be white or colored. For example, a bulb or an alarm can be connected to the circuit. Other equivalent means for generating such signal are readily known by those skilled in the art.

If the production of sound is employed as the electric signal, it will not be necessary to provide a means of seeing the signal. Sound of course has the disadvantage that if it is loud enough it might disturb the baby, and hence, the use of light as the indicating means might be the preferred way of employing the electrical species of the invention. To prevent disturbing the baby and also for the reasons advanced with the chemical species, it might be preferable in the electrical species as well to have the indicating means in a layer of the diaper which does not contact the skin.

Exemplary exogenous electrolytes include sodium and potassium chloride, copper sulfate, boric acid, potassium hydrogen phthalate, or potassium dihydrogen phosphate. The exogenous electrolyte can also be an electrolyte naturally found in urine or other human excretions. Alternatively, an electrolyte might not be needed if the endogenous electrolytes in natural urine are sufficient to complete the circuit and generate the signal.

As is well-known, ionization of the electrolyte will be increased with dilution (up to a point) which will thereby make the signal stronger, e.g., a louder beep or a stronger light, which can be used as a means for determining when the diaper should be changed.

As conducting wires, conductive polymers and metal-polymer blends as described by Hudgin et al. in U.S. Pat. Nos. 4,533,685 and 4,582,872 can be used, the complete disclosures of which are hereby incorporated by reference and relied upon.

It will be apparent to those of ordinary skill in the art that various changes and modifications can be made therein without departing from the spirit and scope therefrom.

What is claimed is:

1. A multi-layered storage container that indicates the presence of acid gases by colored change, comprising:
   (a) at least one layer of a gas-porous plastic wherein the gas is selected from the group consisting of carbon dioxide, hydrogen chloride, sulfur dioxide and sulfur trioxide and wherein the plastic is selected from the group consisting of a hydrocarbon polymer of a mono-olefin having two to six carbon atoms, ethylene-mono-olefin copolymer, linear polyester, polycarbonate and polystyrene,
   (b) at least one layer of a gas-barrier polymer, said gas-barrier polymer being decomposable to form an acid gas,
   wherein the innermost layer of said multi-layer storage container is made of said gas-porous plastic, and wherein at least one layer of said multi-layer storage container is provided with a color-changing indicator which changes color to show the presence of the acid gas formed by the decomposition of said gas-barrier polymer.

2. The multi-layered storage container of claim 1, wherein said gas-porous plastic is selected from the group, consisting of polyethylene, polypropylene, polyethylene terephthalate and polystyrene.

3. The multi-layered storage container of claim 1, wherein the plastic is selected from the group consisting polyethylene, polypropylene, ethylene-mono-olefin copolymer, polyamylene, linear polyester, polycarbonate and polystyrene.

4. The multi-layered storage container of claim 1, wherein said gas-porous plastic is a hydrocarbon polymer of a mono-olefin having 2 to 6 carbon atoms or polystyrene.

5. The multi-layered storage container of claim 1, wherein said gas-barrier polymer is selected from the group consisting of vinylidene chloride polymer and vinyl chloride polymer.

6. The multi-layered storage container of claim 5, wherein said vinylidene chloride polymer is selected from the group consisting of polyvinylidene chloride, vinylidene chloride-acrylonitrile copolymer and vinylidene chloride-vinyl chloride copolymer.

7. The multi-layered storage container of claim 5, wherein said vinyl chloride polymer is selected from the group consisting of polyvinyl chloride and vinyl chloride-vinyl acetate copolymer.

8. The multi-layered storage container of claim 1, wherein said color-changing indicator is selected from the group comprising litmus, methyl orange, bromphenol red or bromthymol blue.

9. The multi-layered storage container of claim 1, wherein said color-changing indicator shows the presence of acidic gases selected from the group comprising carbon dioxide, hydrogen chloride, sulfur dioxide or sulfur trioxide.

10. The multi-layered storage container of claim 1, wherein the color-changing indicator is present in the innermost gas porous-plastic layer.

11. The multi-layered storage container of claim 10 containing in a non-acidic atmosphere an article which is sensitive to acidic gases.

12. The multi-layered storage container of claim 11, wherein said article is a philatelic item, photograph or museum piece.

13. The multi-layered storage container of claim 1, wherein the container contains a museum piece.

14. The multi-layered storage container of claim 1, wherein the container contains a photograph.

15. The multi-layered storage container of claim 1, where in the container contains a philatelic item.

* * * * *